(12) United States Patent
Kiyota

(10) Patent No.: US 8,478,008 B2
(45) Date of Patent: Jul. 2, 2013

(54) CULTURE APPARATUS, CULTURE INFORMATION MANAGEMENT METHOD, AND COMPUTER READABLE MEDIUM STORING PROGRAM OF SAME

(75) Inventor: Yasujiro Kiyota, Tokyo (JP)

(73) Assignee: Nikon Corporation, Tokyo (JP)

( * ) Notice: Subject to any disclaimer, the term of this patent is extended or adjusted under 35 U.S.C. 154(b) by 136 days.

(21) Appl. No.: 12/709,017

(22) Filed: Feb. 19, 2010

(65) Prior Publication Data

US 2010/0208960 A1 Aug. 19, 2010

Related U.S. Application Data

(63) Continuation of application No. PCT/JP2008/002344, filed on Aug. 28, 2008.

(30) Foreign Application Priority Data

Sep. 3, 2007 (JP) ................................ 2007-227681

(51) Int. Cl.
*G06K 9/00* (2006.01)
(52) U.S. Cl.
USPC ........................................................ 382/128
(58) Field of Classification Search
USPC ........................... 382/128, 190, 130; 715/703
See application file for complete search history.

(56) References Cited

U.S. PATENT DOCUMENTS

| | | | | |
|---|---|---|---|---|
| 7,816,126 B2 * | 10/2010 | Kagayama et al. | ........ | 435/288.7 |
| 2004/0241832 A1 * | 12/2004 | Muraki et al. | ............. | 435/287.1 |
| 2005/0112542 A1 | 5/2005 | West | | |
| 2005/0288867 A1 * | 12/2005 | Kuno | ............................... | 702/19 |
| 2008/0244397 A1 * | 10/2008 | Ferlitsch | ........................ | 715/703 |

FOREIGN PATENT DOCUMENTS

| | | | |
|---|---|---|---|
| JP | 2004344049 | * | 12/2004 |
| JP | A-2004-344049 | | 12/2004 |
| JP | 2007-20422 | * | 2/2007 |
| JP | A-2007-20422 | | 2/2007 |
| JP | A-2007-20553 | | 2/2007 |
| JP | A-2007-121106 | | 5/2007 |
| JP | 2007-174963 | * | 7/2007 |
| WO | WO 2006/005808 A1 | | 1/2006 |
| WO | WO 2006/086489 A1 | | 8/2006 |
| WO | WO 2006/092925 A1 | | 9/2006 |

OTHER PUBLICATIONS

Oct. 14, 2008 International Search Report issued in corresponding Internationa Patent Application No. PCT/JP2008/002344.
Mar. 30, 2010 International Preliminary Report on Patentability issued in corresponding International Patent Application No. PCT/JP2008/002344 (with translation).

*Primary Examiner* — Nancy Bitar
(74) *Attorney, Agent, or Firm* — Oliff & Berridge, PLC

(57) ABSTRACT

A temperature-controlled room accommodates an incubation container incubating a sample and maintains the inside thereof in a predetermined environment condition. An imaging section generates data of a plurality of observing images. An image analyzing section performs an image analyzing process on the data of the plurality of observing images obtained by imaging the incubation container at different times. Image analyzing data generated by the image analyzing section includes morphological information which indicates incubation states of the samples and rate-of-change information regarding the morphological information. A search processing section conducts a search for the incubation container which meets the first searching condition and the second searching condition based on the image analyzing data.

9 Claims, 10 Drawing Sheets

OTHER PUBLICATIONS

Database WPI, Week 200674, Thomson Scientific, London, GB; AN 2006-717181 (XP-002667934).

Feb. 6, 2012 Supplementary European Search Report issued in European Patent Application No. 08 82 9287.

* cited by examiner

```
┌─────────────────────────────────────────────────────┐
│ ┌──────────┐                                        │
│ │ USER:AAA │    ┌──────────────────────────────┐    │
│ └──────────┘    │  SEARCHING CONDITION INPUT   │    │
│                 │ FIRST SEARCHING CONDITION :  │    │
│ ┌──────────┐    │ ┌──────────────────────────┐ │    │
│ │CONTAINER │    │ │NUMBER OF CELLS AFTER     │ │    │
│ │CARRYING OUT│  │ │DIFFERENTIATION INDUCTION │ │    │
│ └──────────┘    │ └──────────────────────────┘ │    │
│                 │ UPPER LIMIT ┌──┐ LOWER LIMIT ┌──┐│    │
│ ┌──────────┐    │   VALUE :   └──┘   VALUE :  └──┘│    │
│ │TEMPERATURE:─│ │                              │    │
│ │HUMIDITY   :─│ │ SECOND SEARCHING CONDITION : │    │
│ │CO2        :─│ │ ┌──────────────────────────┐ │    │
│ └──────────┘    │ │INCREASE RATE OF CELLS AFTER│ │   │
│                 │ │DIFFERENTIATION INDUCTION │ │    │
│                 │ └──────────────────────────┘ │    │
│                 │ UPPER LIMIT ┌──┐ LOWER LIMIT ┌──┐│    │
│                 │   VALUE :   └──┘   VALUE :  └──┘│    │
│ ┌──────────┐    │                              │    │
│ │ DETAILED │    └──────────────────────────────┘    │
│ │ SETTING  │                                        │
│ └──────────┘                                        │
└─────────────────────────────────────────────────────┘
```

FIG.12

```
┌─────────────────────────────────────────────────────┐
│ ┌──────────┐   SEARCH RESULT                        │
│ │ USER:AAA │   ┌──────────────┐                     │
│ └──────────┘   │  24Well A3   │                     │
│                └──────────────┘                     │
│ ┌──────────┐                                ICON    │
│ │CONTAINER │   ┌──────────────┐         ╱           │
│ │CARRYING OUT│ │  6Well B1    │────────            │
│ └──────────┘   └──────────────┘                     │
│                                                     │
│ ┌──────────┐   ┌──────────────┐                     │
│ │TEMPERATURE:─│ │  6Well C4    │                    │
│ │HUMIDITY   :─│ └──────────────┘                    │
│ │CO2        :─│         ·                           │
│ └──────────┘           ·                            │
│                        ·                            │
│                                                     │
│ ┌──────────┐                                        │
│ │ DETAILED │                                        │
│ │ SETTING  │                                        │
│ └──────────┘                                        │
└─────────────────────────────────────────────────────┘
```

CULTURE APPARATUS, CULTURE INFORMATION MANAGEMENT METHOD, AND COMPUTER READABLE MEDIUM STORING PROGRAM OF SAME

CROSS REFERENCE TO RELATED APPLICATION

This application is a continuation application of International Application PCT/JP2008/002344, filed Aug. 28, 2008, designating the U.S., and claims the benefit of priority from Japanese Patent Application No. 2007-227681, filed on Sep. 3, 2007, the entire contents of which are incorporated herein by reference.

BACKGROUND

1. Field

The present application relates to a culture apparatus and a related technique for incubating a sample in a temperature-controlled room adjusted in a predetermined environment condition.

2. Description of the Related Art

Conventionally, there is known a culture apparatus incubating a cell within an incubation container in a temperature-controlled room which is maintained in a predetermined atmosphere. Further, for an example of the culture apparatus, Japanese Unexamined Patent Application Publication No. 2007-20422 discloses a configuration to record analysis information which is obtained by analyzing the observation result of an incubated cell, together with an image, and to display the analysis information together with the image on a monitor.

However, the conventional technique does not perform information management of the image or the like according to the analysis information, and it is extremely troublesome for a user to search for and identify an incubation container which satisfies a predetermined condition. In particular, when incubating cells using plural incubation containers in the temperature-controlled room, since there are huge volume of images and analysis information which show incubation states, it is required to further improve its search performance.

BRIEF DESCRIPTION OF THE DRAWINGS

FIG. 12 is a diagram showing an example of an input screen of a searching condition.

FIG. 13 is a diagram showing an example of a search result screen.

DETAILED DESCRIPTION OF THE EMBODIMENT (Explanation of an Incubator Configuration)

Figure 1:
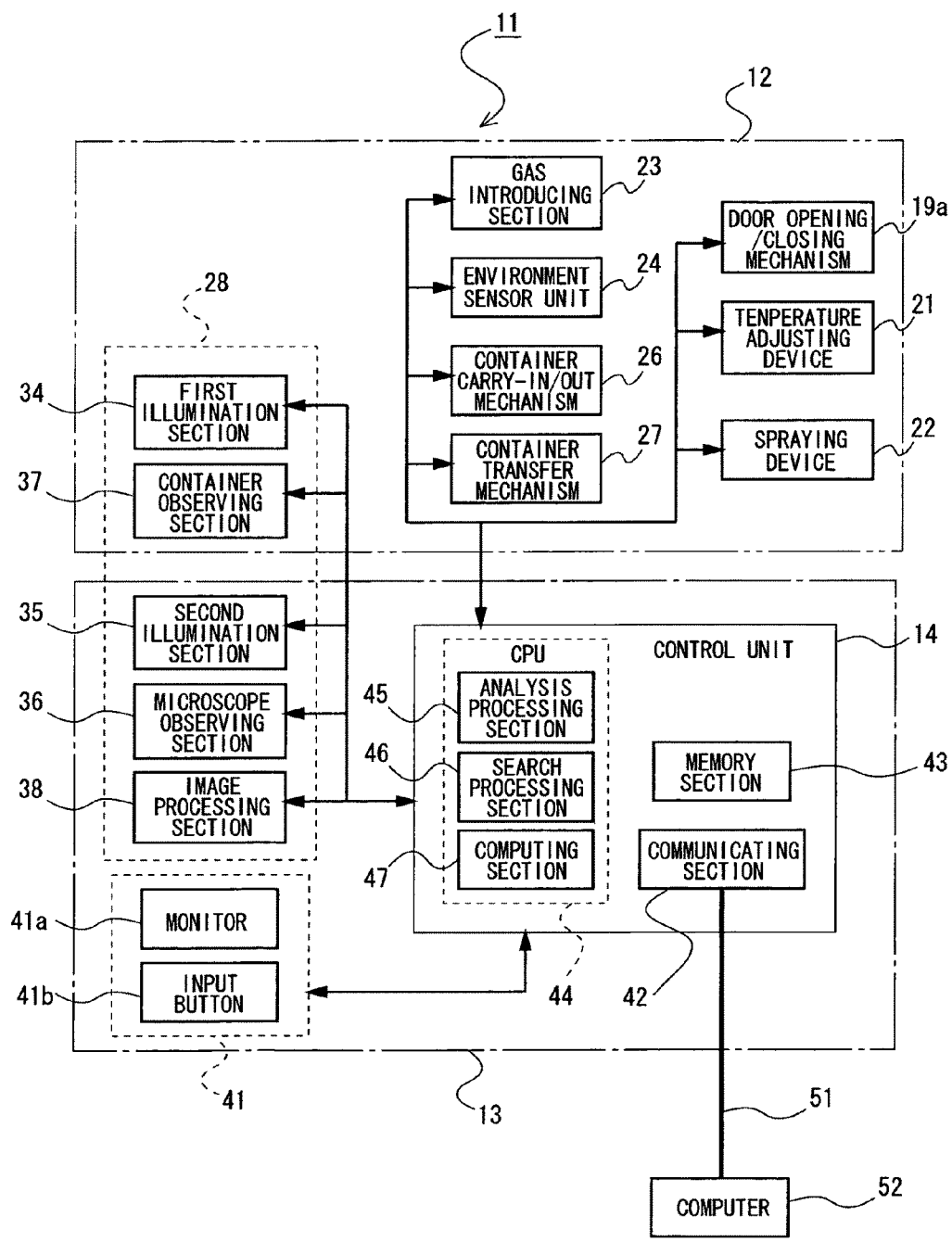
FIG. 1 is a block diagram of an incubator of an embodiment.
Figure 2:
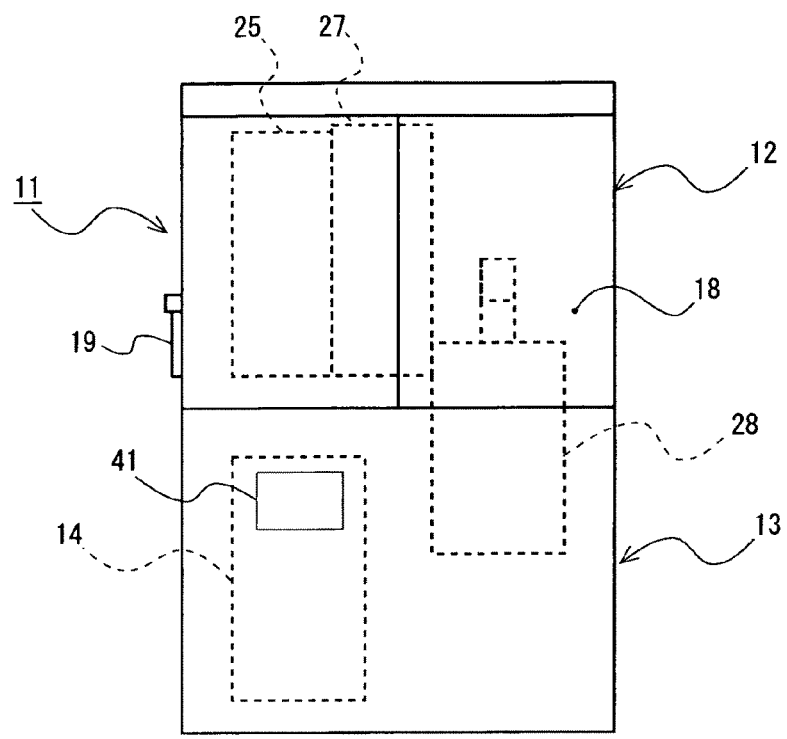
FIG. 2 is a front view of the incubator of the embodiment.
Figure 3:
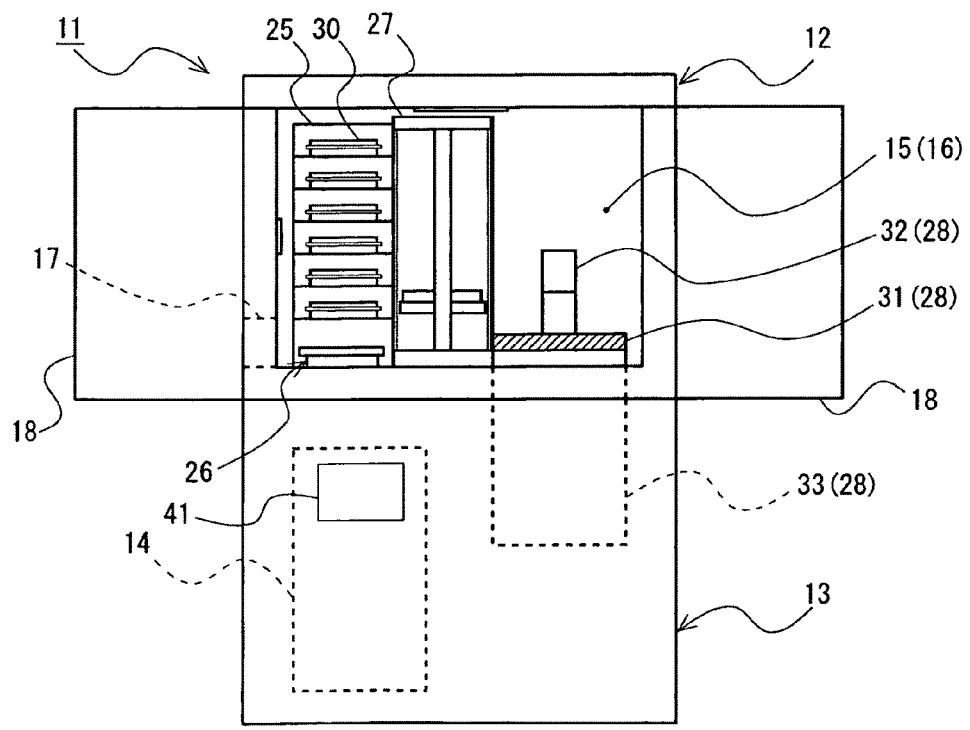
FIG. 3 is a diagram showing an open state of the front door in FIG. 2.

Hereinafter, an incubator configuration of an embodiment will be described in detail with reference to the drawings. FIG. 1 is a block diagram of an incubator in an embodiment. Further, FIG. 2 and FIG. 3 are front views of the incubator in the embodiment.

An incubator 11 of the embodiment includes a first enclosure 12 performing incubation of a biological sample and a second enclosure 13 accommodating a control unit 14. The first enclosure 12 is disposed on the second enclosure 13 in an assembled state of the incubator 11.

First, a configuration outline of the first enclosure 12 will be described. A temperature-controlled room 15 covered by a heat-insulating material is formed inside the first enclosure 12. This temperature-controlled room 15 communicates with the outside by a front opening 16 formed on a front side of the first enclosure 12 and a carry-in/out opening 17 formed on the left lateral side of the first enclosure 12 in FIG. 2 and FIG. 3. The front side opening 16 of the first enclosure 12 is closed by a double front door 18 in an openable and closable manner. Further, the carry-in/out opening 17 of the first enclosure 12 is closed by an automatic slide door 19 in an openable and closable manner. Note that the size of the carry-in/out opening 17 is set to a size allowing an incubation container (30) to pass therethrough. Meanwhile, an opening 20 is formed on the bottom side of the first enclosure 12 at a right position in the front view. Note that an observing unit (28) to be described below is disposed in the temperature-controlled room 15 via the opening 20.

Further, the wall side of the temperature-controlled room 15 includes each of a temperature adjusting device 21, a spraying device 22, a gas introducing section 23, and an environment sensor unit 24.

The temperature adjusting device 21 includes a Peltier element and heats or cools the temperature-controlled room 15 by the Peltier effect. The spraying device 22 performs spraying in the temperature-controlled room 15 to adjust humidity within the temperature-controlled room 15. The gas introducing section 23 is coupled to a carbon-dioxide bomb (not shown in the drawing). This gas introducing section 23 introduces carbon-dioxide into the temperature-controlled room 15 and thereby adjusts a carbon-dioxide concentration within the temperature-controlled room 15. The environment sensor unit 24 detects each of temperature, humidity, and a carbon-dioxide concentration within the temperature-controlled room 15.

In the assembled state of the incubator 11, each of a stocker 25, a container carry-in/out mechanism 26, a container transfer mechanism 27, and a part of the observing unit 28 is disposed within the temperature-controlled room 15.

The stocker 25 is disposed on the left side of the temperature-controlled room 15 in the front view of the first enclosure 12. The stocker 25 has a plurality of shelves and can accommodate an incubation container 30 on each of the shelves. Further, the bottom step of the stocker 25 corresponds to the position of the carry-in/out opening 17 of the first enclosure 12. Additionally, in a space of the bottom step of the stocker 25, the container carry-in/out mechanism 26 is disposed for carrying in or carrying out the incubation container 30.

The container transfer mechanism 27 is disposed at the center of the temperature-controlled room 15 in the front view of the first enclosure 12. The container transferring mechanism 27 performs the delivery and receipt of the incubation container 30 between the stocker 25, the container carry-in/out mechanism 26, and the observing unit 28.

The observing unit 28 is disposed on the right side of the temperature-controlled room 15 in the front view of the first enclosure 12. This observing unit 28 is disposed to be fitted in the opening 20 on the bottom of the first enclosure 12. This observing unit 28 includes a sample stage 31, an arm 32 extending above the sample stage 31, and a main body part 33. Then, while the sample stage 31 and the arm 32 are disposed within the temperature-controlled room 15 of the first enclosure 12, the main body part 33 is accommodated in the second enclosure 13.

Figure 4:
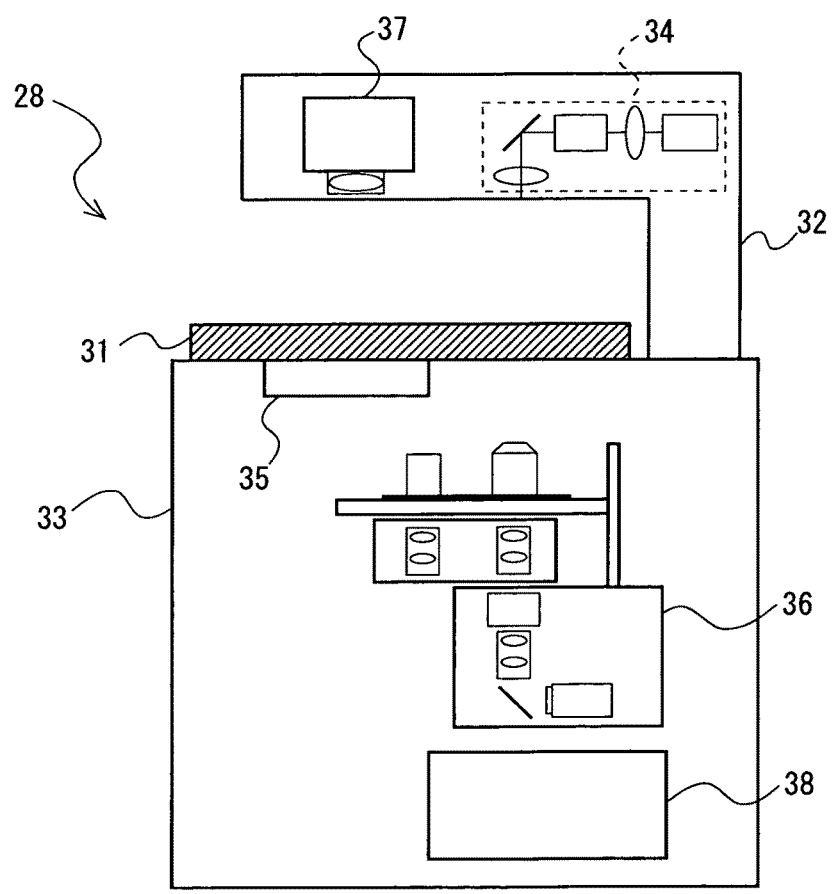
FIG. 4 is a schematic diagram showing a configuration of an observing unit.

FIG. 4 is a schematic diagram showing a configuration of the observing unit 28. The observing unit 28 includes the sample stage 31, a first illumination section 34 and a second illumination section 35, a microscope observing section 36, a container observing section 37, and an image processing section 38.

The sample stage 31 is made of a translucent material and mounts the incubation container 30 thereon. This sample stage 31 is configured to be movable in the horizontal direction (X direction and Y direction), and can adjust the position of the incubation container 30 against the microscope observing section 36 and the container observing section 37.

Further, the first illumination section 34 is disposed within the arm 32 and illuminates the incubation container 30 from above the sample stage 31. On the other hand, the second illumination section 35 is included within the main body part 33 and illuminates the incubation container 30 from below the sample stage 31.

The microscope observing section 36 is included within the main body part 33 and is configured in combination of a microscope and an imaging device.

The container observing section 37 is accommodated in the arm 32 and has an imaging optical system and an imaging sensor (neither shown in the drawing). This container observing section 37 takes a whole observing image of the incubation container 30 with the illumination light of the second illumination section 35.

The image processing section 38 performs A/D conversion on an image output from each of the microscope observing section 36 and the container observing section 37. Then, the image processing section 38 performs various kinds of image processing (color interpolation processing, gradation conversion processing, white balance adjustment, etc.) on each of these image outputs to generate image data.

Next, a configuration outline of the second enclosure 13 will be described. The second enclosure 13 accommodates the main body part 33 of the observing unit 28 and the control unit 14. Further, on the front side of the second enclosure 13 is disposed an operation panel 41 provided with a monitor 41a and an input button 41b.

Here, the control unit 14 is coupled with each of a door opening/closing mechanism 19a of the automatic door 19, the temperature adjusting device 21, the spraying device 22, the gas introducing section 23, the environment sensor unit 24, the container carry-in/out mechanism 26, the container transfer mechanism 27, the observing unit 28, and the monitor 41a and input button 41b of the operation panel 41.

The control unit 14 collectively controls the respective sections of the incubator 11 according to a predetermined program. For example, the control unit 14 maintains the inside of the temperature-controlled room 15 in a predetermined environment condition by controlling each of the temperature adjusting device 21, the spraying device 22, the gas introducing section 23, and the environment sensor unit 24. Further, the control unit 14 automatically executes an observing sequence of the incubation container 30 by controlling the observing unit 28 and the container transfer mechanism 27 according to a predetermined observing schedule.

Here, the control unit 14 includes a communicating section 42, a memory section 43, and a CPU 44. Note that each of the communicating section 42 and the memory section 43 is coupled to the CPU 44.

The communicating section 42 carries out data transmission/reception with a computer 52 located outside the incubator 11 via a wireless or wired communication line 51.

The memory section 43 is configured with a nonvolatile storage medium such as a hard disk, a flash memory, or the like. This memory section 43 records management data regarding each of the incubation containers 30 accommodated in the stocker 25. Further, the memory section 43 records the whole observing image data, an image file of a microscope observing image to be described below, and the like.

Here, the above management data includes (a) identification data indicating each of the incubation containers 30, (b) an accommodation position of the incubation container 30 on the stocker 25, (c) a kind and shape of the incubation container 30 (well plate, dish, flask, or the like), (d) a kind of a sample to be incubated in the incubation container 30, (e) a kind of coating on an adhesion surface of the incubation container 30 (collagen coat or hydrophilic processing), (f) an observing schedule of the incubation container 30, etc. Note that, for the incubation container 30 capable of incubating samples at the same time in a plurality of small containers such as the well plate, the management data is generated for each of the small containers.

The CPU 44 is a processor executing various kinds of computational processing of the control unit 14. This CPU 44 functions as an analysis processing section 45, a search processing section 46 and a computing section 47 by executing a program.

The analysis processing section 45 performs an image analyzing process on the microscope observing image data taken by the microscope observing section 36 to generate image analyzing data indicating an incubation state of a sample (cell line or the like) using the microscope observing image. Then, the analysis processing section 45 generates meta data including the identification data indicating the shot incubation container 30 and the above image analyzing data, and generates the image file of the microscope observing image by associating this meta data with the microscope observing image data.

The search processing section 46 searches the memory section 43 for the image file of the microscope observing image which meets a predetermined searching condition, by referring to the meta data in the image file of the microscope observing image.

The computing section 47 obtains a temporal change amount of a parameter regarding the image analyzing data using respective plural sets of the image analyzing data obtained by imaging a specific incubation container at different times. Further, the computing section 47 also can obtain a predictive value of the parameter for the specific incubation container after that, using the parameter change amount obtained from the image analyzing data.

(Explanation of an Observing Operation in the Incubator)

Figure 5:
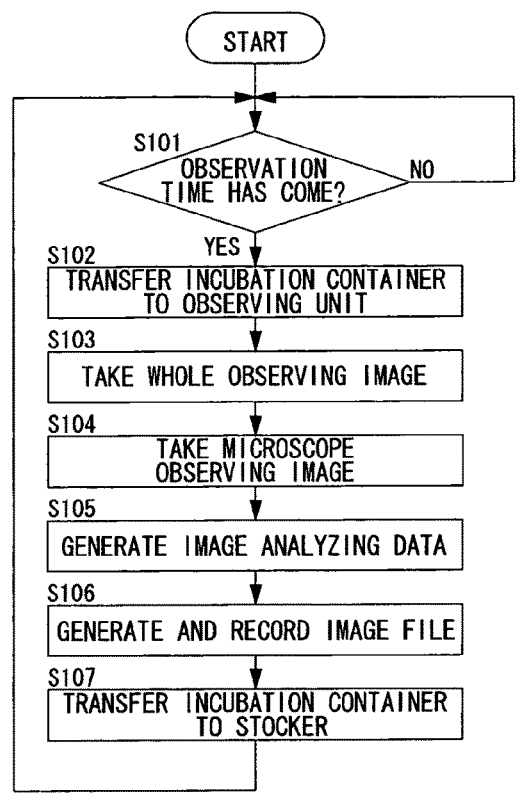
FIG. 5 is a flowchart illustrating an observing operation of the incubator in the embodiment.

Hereinafter, an example of an observing operation in the incubator of an embodiment will be described with reference to a flowchart of FIG. 5. Here, in the following example, there will be described a case in which the incubation container 30 carried into the temperature-controlled room 15 is time-lapse-observed according to a registered observing schedule. Note that it is assumed that the incubation container 30 accommodates a cell line together with a culture medium.

Step S101: The CPU 44 determines whether observation start time has come or not for any of the incubation containers 30, by comparing the observing schedule registered in the memory section 43 with present time. If the observation start time has come (YES side), the process goes to S102. On the other hand, if the observation time has not come for any of the incubation containers 30 (NO side), the CPU 44 waits for the next time of the observing schedule.

Step S102: The CPU 44 instructs the container transfer mechanism 27 to transfer the incubation container 30 corresponding to the observing schedule. Then, the container transfer mechanism 27 carries the indicated incubation container 30 out of the stocker 25 and mounts it on the sample stage 31 of the observing unit 28.

Step S103: The CPU 44 instructs the observing unit 28 to take the whole observing image. The observing unit 28 turns on the second illumination section 35 to illuminate the incubation container 30, and also takes the whole observing image of the incubation container 30 with the imaging sensor of the container observing section 37.

Step S104: The CPU 44 instructs the observing unit 28 to take the microscope observing image. The observing unit 28 turns on the first illumination section 34 to illuminate the incubation container 30, and also takes the microscope observing image of the incubation container 30 with the imaging sensor of the microscope observing section 36. At this time, the observing unit 28 takes the microscope observing image in a condition set by a user (magnification of an objective lens, observation point in the container, number of frames, etc.) according to the observing schedule. After that, the image processing section 38 performs predetermined image processing on the microscope observing image data. Note that, in the embodiment, an image of the sample observed in a phase contrast of transmission light is taken as the microscope observing image.

Step S105: The analysis processing section 45 of the CPU 44 performs an image analyzing process on the microscope observing image data (S104) to generate the image analyzing data. Specifically, the analysis processing section 45 carries out the following image analyzing processes of (1) to (3).

(1) Computation of a Standard Statistical Amount Regarding Brightness

When the image of the incubated cell is taken with a phase contrast microscope, a part of the cell becomes comparatively darker in the image while a part except the cell becomes brighter, and a brightness difference is caused. Accordingly, by using the image analyzing data focused on the brightness of the microscope observing image, it becomes possible to determine a size or the like of a region possessed by the cell in the image.

Then, the analysis processing section 45 obtains "average brightness value of the microscope observing image", "standard deviation of brightness in the microscope observing image", "maximum value and minimum value of brightness in the microscope observing image", "possession area of a region having brightness equal to or higher than a predetermined brightness on the microscope observing image", and "brightness histogram of the microscope observing image", as the image analyzing data by respective publicly known methods.

(2) Acquisition of Cell Form Information

When focusing on the form of the cell taken in the microscope observing image, it becomes possible to determine the state of an individual cell. For example, when the shape of the cell is close to a circle, it can be determined that the cell is in a floating state or the cell is in a normal state. On the other hand, when the shape of the cell is close to an ellipsoid, it can be determined that the cell in the observation is in a state before or after division or the state of the cell is deteriorated. Further, when the cell is in a coupled state, it can be determined that the cell is in a division state or in a simple coupling state.

Then, the analysis processing section 45 obtains each of "circularity of a cell", "ellipticity of a cell", "non-circularity of a cell", "number of single cells", "number of coupled cells", "cell size", and "cell size distribution", as the image analyzing data.

Here, "circularity of a cell" indicates the number of cells, each having a presumably true circle shape, among the cells included in the microscope observing image. "Ellipticity of a cell" indicates the number of cells, each having a presumably ellipsoid shape, among the cells included in the microscope observing image. "Non-circularity of a cell" indicates how far the shape of the cell is apart from a true circle, and is a parameter for digitalizing the number of cells each not corresponding to a true circle or an ellipsoid, among the cells included in the microscope observing image. "Number of single cells" and "number of coupled cells" indicate the number of single cells and the number of coupled cells included in the microscope observing image, respectively. Further, "cell size" indicates an average value of the sizes of all the cells included in the microscope observing image.

Further, the analysis processing section 45 generates cell morphological information from the microscope observing image by the following method. First, the analysis processing section 45 analyzes the microscope observing image and obtains respective positions and a sum total of the cells included within the imaging region. For example, when the image of the incubated cell is taken with the phase contrast microscope, a halo appears around a periphery of a part having a large phase difference change such as a cell wall. Therefore, the analysis processing section 45 extracts the halo corresponding to the cell wall by an publicly known edge extraction means, and estimates the inside of a closed space surrounded by the edge to be a profile of the cell.

Second, the analysis processing section 45 focuses on the number of nuclei included in the profile of the cell, and obtains each of "number of single cells" and "number of coupled cells". Further, the analysis processing section 45 obtains the size of the individual cell, and computes "cell size" and "cell size distribution".

Third, the analysis processing section 45 categorizes the shape of each cell, and obtains each of "circularity of a cell", "ellipticity of a cell", and "non-circularity of a cell". For example, the analysis processing section 45 extracts a circular shape and an ellipsoidal shape from the profile shapes of the respective cells included in the microscope observing image, using a publicly known algorism such as the Hough transform and the generalized Hough transform. Then the analysis processing section 45 obtains "circularity of a cell" from the number of cells each having a similarity with a circle equal to or higher than a threshold value. Similarly, the analysis processing section 45 obtains "ellipticity of a cell" from the number of cells each having a similarity with an ellipsoid equal to or higher than a threshold value. Then, the analysis processing section 45 obtains "non-circularity of a cell" from the number of cells without similarity with either of the above shapes among the cells included in the microscope observing image. Note that the analysis processing section 45 may presume the cell, which is larger than a size of two cells and has a low circularity of a cell, to be a coupled cell.

(3) Image Untidiness Information

When focusing on the complexity of the cell form taken in the microscope observing image, it becomes possible to determine an activity state of the cell. For example, a cell form change is also caused by the movement of the cell itself in addition to the cell division. By measuring a distribution of barycentric points ("cell barycentric point distribution") in the microscope observing image for the movement of the whole cell, it is possible to specify a cell position at a certain time. Then, by measuring the above cell barycentric point distribution temporally, it becomes possible to obtain a cell movement speed.

Further, by obtaining an area of an individual cell region around the barycentric point ("barycentric point individual area"), it is possible to clarify a relationship between the cell size (colony size) and a position thereof. Then, by measuring the barycentric point individual area temporally, it is possible to determine a cell movement capability from a correlation between the cell size and the movement speed. Moreover, by a distance of the cell profile from the cell barycentric point ("barycentric point-profile distance"), a relationship between the cell size or cell shape and the cell area is clarified. Then, from these sets of data, it is possible to make an indicator of the correlation for the cell form change in the movement.

Further, for a cell extending a dendrite, by extracting the dendrite as a "unique point" and temporally observing the "unique point", it also becomes possible to obtain a correlation between an extension direction of the dendrite and the cell movement.

Figure 6:
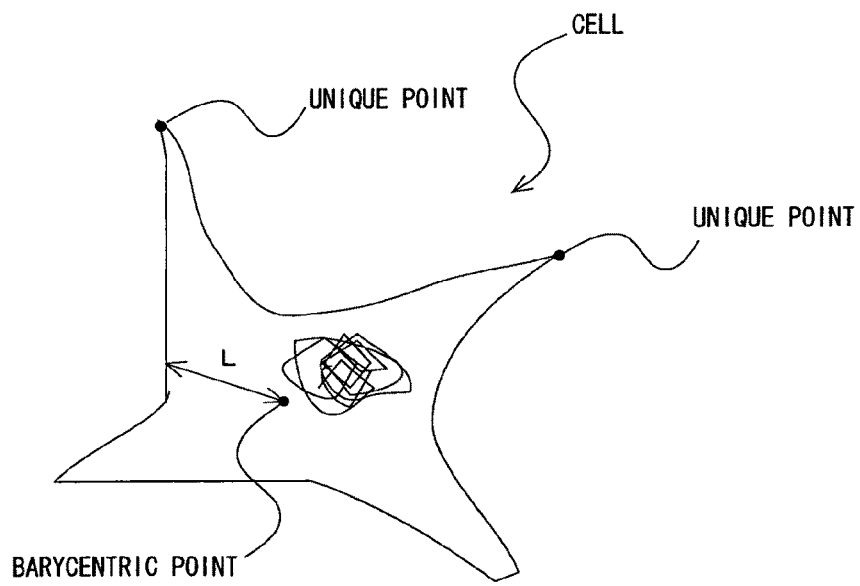
FIG. 6 is an exemplary diagram showing a cell shape and a barycentric point of the cell shape.

Accordingly, the analysis processing section 45 in the embodiment obtains each of the "cell barycentric point distribution", "barycentric point individual area, "barycentric point-profile distance", and "unique point" as the image analyzing data. For example, the analysis processing section 45 obtains respective barycentric points for a group of the cells using a publicly known barycentric point computation algorithm. Then the analysis processing section 45 determines a distribution state of the barycentric points in the microscope observing image to be "cell barycentric point distribution". Further, the analysis processing section 45 determines "barycentric point individual area" by associating each barycentric point with a cell size. Moreover, the analysis processing section 45 connects the barycentric point and a point on the cell profile with a straight line L for each cell and determines a sum total length of the straight lines L along the whole cell profile to be the "baricentric point-profile distance". Further, the analysis processing section 45 obtains an end point of the cell profile and determines the end point to be "unique point" when the distance between this end point and the barycentric point is equal to or larger than a threshold value (refer to FIG. 6).

Step S106: The analysis processing section 45 of the CPU 44 adds the meta data including the image analyzing data (S105) to the microscope observing image data (S104) to generate the image file of the microscope observing image. After that, the CPU 44 records the image file of the microscope observing image in the memory section 43.

Here, the image file of the microscope observing image records the following data as the meta data: (1) identification data of the incubation container 30, (2) imaged date and time, (3) environment of the temperature-controlled room 15 at the time of imaging (temperature, humidity, $CO_2$ concentration), (4) objective lens magnification of the microscope, (5) imaged position in the incubation container 30 (center of the container or the like), (6) illumination wavelength and illumination intensity, and (7) image analyzing data (obtained in S105).

Step S107: The CPU 44 instructs the container transfer mechanism 27 to transfer the incubation container 30 after completing the microscope observing image. Then, the container transfer mechanism 27 transfers the indicated incubation container 30 from the sample stage 31 of the observing unit 28 to a predetermined accommodation position of the stocker 25, and the observation sequence is terminated and the process returns to S101. With that, the explanation of the flowchart of FIG. 5 is completed.

(Explanation of Culture Information Search Processing)

Next, an example of culture information search processing in the incubator of an embodiment will be described with reference to a flowchart if FIG. 7. Here, the culture information search processing of the embodiment is carried out by the control unit 14 of the incubator 11. Further, the user carries out various operations for the control unit 14 from the operation panel 56 of the incubator 11 or from the computer 52 coupled to the incubator 11.

Step S201: The CPU 44 of the control unit 14 activates a sequence program for the search processing in response to a user operation. At this time, the CPU 44 causes the monitor 41a of the operation panel 41 (or monitor of the computer 52) to display a menu screen (not shown in the drawing) of the search processing capable of input in the GUI (Graphical User Interface) format.

Here, on the menu screen of the search processing, the user can input a searching condition into the CPU 44 for searching the memory section 43 for the incubation container or the microscope observing image which satisfies a predetermined condition. In an embodiment, the following items can be selected on the menu screen as the above searching condition: (1) imaging time, (2) possession area of an incubated cell, (3) ratio of a single cell to a two-coupled cell among incubated cells, (4) barycentric point individual area, (5) rate of change of an incubated cell possession area, (6) rate of change in a ratio of a single cell to a two-coupled cell, and (7) rate of change of a barycentric point individual area. Note that, when the above item (1) "imaging time" is selected, the user can designate a range of the imaging time on the menu screen for narrowing down a search range. The above conditions (2) to (4) are searching conditions regarding the cell form. Further, the above conditions (5) to (7) include searching conditions regarding the cell form and searching conditions regarding the rate of change of the cell form.

Step 202: The search processing section 46 of the CPU 44 searches for the image file in the memory section 43 using the searching condition designated by the user in S201 as a key. In the following, the processing of the CPU 44 will be specifically described for each of the searching conditions.

(1) Case of the Searching Condition "Imaging Time"

In this case, the search processing section 46 refers to the meta data of "imaging date and time" included in all the image files. Then, the search processing section 46 extracts the microscope observing image taken in an imaging time range designated by the user and causes the monitor 41a of the operation panel 41 (or monitor of the computer 52) to display a search result list (not shown in the drawing). Thereby, the user can easily identify and browse the microscope observing image taken at a predetermined time among the many microscope observing images.

(2) Case of the Searching Condition "Possession Area of an Incubated Cell"

In this case, first the search processing section 46 designates the latest image files as search objects for the incubation containers 30, respectively, using the identification data. Next, the search processing section 46 obtains the possession area data of the incubated cell in each of the incubation containers 30 by referring to the meta data of "possession area of a region equal to or brighter than a predetermined brightness on the microscope observing image" included in the image file of the search object. Note that the size of the region equal to or brighter than the predetermined brightness indicated by the meta data corresponds to the size of a region where the incubated cell does not exist. Accordingly, as the region equal to or brighter than the predetermined brightness indicated by the meta data becomes smaller, the possession area of the incubated cell becomes larger.

Then, the search processing section 46 causes the monitor 41a or the like to display a list screen which shows the possession area of the incubated cell for each of the incubation containers 30 in the temperature-controlled room 15.

Figure 8:
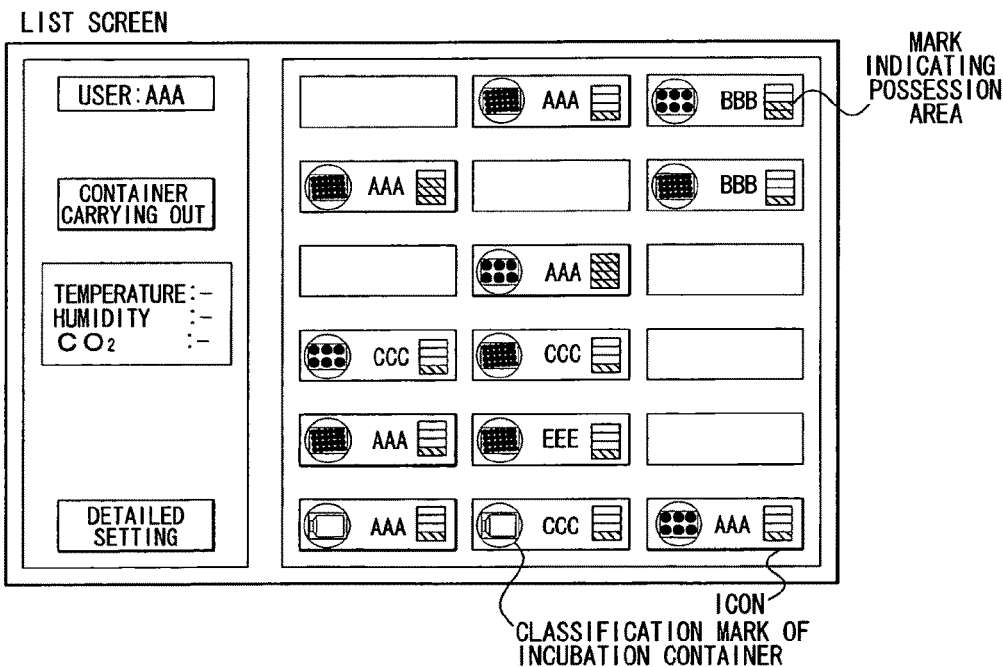
FIG. 8 is a diagram showing an example of a list screen showing a search result of an incubated cell possession area.

FIG. 8 shows an example of the list screen showing the search result of the incubated cell possession area. The list screen of FIG. 8 displays the incubation container 30 in the temperature-controlled room 15 by a GUI (Graphical User Interface) format icon. The arrangement of the icons on this list screen corresponds to the arrangement of the incubation containers 30 in the stocker 25.

Further, each of the icons displays a mark representing the possession area of the incubated cell. Thereby, the user can easily grasp whether confluence exists or not and the like at the time of imaging of the microscope observing image, from the present possession area of the incubated cell in each of the incubation containers 30 by the above mark on the list screen. Note that, when the user sets a threshold value of "possession area of an incubated cell" in the searching, the CPU 44 may not display the icon on the list screen of FIG. 8 for the incubation container 30 which has the incubated cell possession area equal to or smaller than the threshold.

(3) Case of the Searching Condition "Ratio of a Single Cell to a Two-Coupled Cell Among Incubated Cells"

In this case, first the search processing section 46 designates the latest image files as search objects for the incubation containers 30, respectively, using the identification data. Next, the search processing section 46 computes "ratio of a single cell to a two-coupled cell among incubated cells" from the meta data of "number of single cells" and "number of coupled cells" included in the image file of the search object. Then, the search processing section 46 causes the monitor 41a or the like to display a list screen which shows ratio of a single cell to a two-coupled cell among incubated cells for each of the incubation containers 30 in the temperature-controlled room 15. Note that the list screen in this case has a display format approximately in common with that of FIG. 8 and explanation will be omitted. By such display of "ratio of a single cell to a two-coupled cell among incubated cells", the user can easily grasp a state of the cell division at the time of imaging of the microscope observing image in each of the incubation containers 30.

(4) Case of the Searching Condition "Barycentric Point Individual Area"

In this case, first the search processing section 46 designates the latest image files as search objects for the incubation containers 30, respectively, using the identification data. Next, the search processing section 46 reads in the meta data of "barycentric point individual area" included in the image file of the search object, and computes an area ratio of a cell cluster (colony) and a cell except the cell cluster. Then, the search processing section 46 causes the monitor 41a or the like to display a list screen which shows a ratio of the barycentric point individual area for each of the incubation containers 30 in the temperature-controlled room 15. Note that the list screen in this case has a display format approximately in common with that of FIG. 8 and explanation will be omitted. By such a display of "barycentric point individual area", the user can easily grasp a state of the colony formation at the time of imaging of the microscope observing image in each of the incubation containers 30.

(5) Case of the Searching Condition "Rate of Change of an Incubated Cell Possession Area"

In this case, first the search processing section 46 designates the plurality of image files taken temporally for the same image object (e.g., first image file and last (latest) image file) as search objects for each of the incubation containers 30 using the identification data.

Next, the computing section 47 computes the rate of change of the incubated cell possession area in each of the incubation containers 30 using the plural meta data sets of "possession area of a region equal to or brighter than a predetermined brightness on the microscope observing image" included in the respective image files of the search objects. Then, the search processing section 46 causes the monitor 41a or the like to display a list screen which shows the rate of change of the incubated cell possession area for each of the incubation containers 30 in the temperature-controlled room 15. The list screen in this case has a display format approximately in common with that of FIG. 8 and explanation will be omitted. By such display of "rate of change of an incubated cell possession area", the user can easily perform the evaluation of a temporal incubation state (e.g., determination for medicine screening) of a cell in each of the incubation containers 30.

Figure 9:
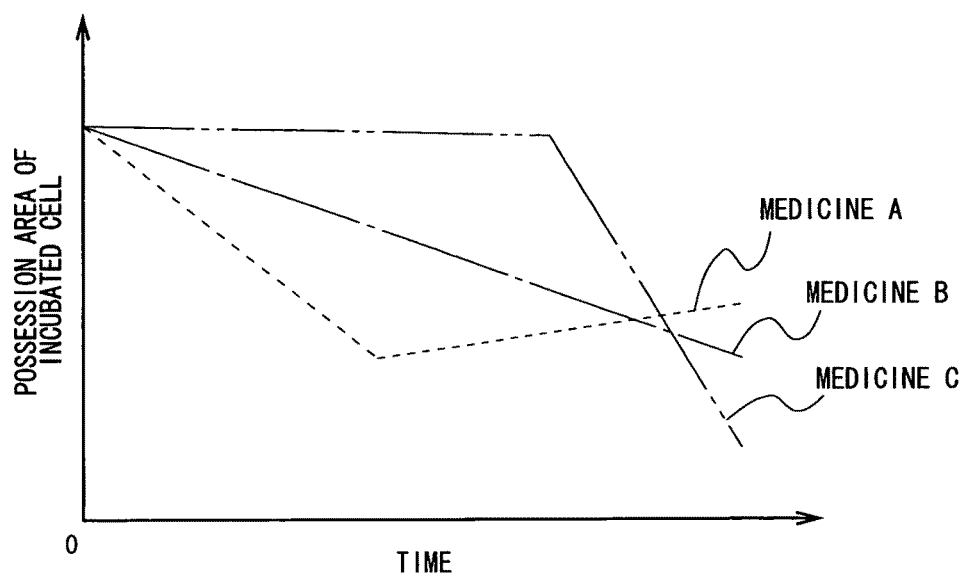
FIG. 9 is a diagram showing an example of a rate-of-change graph of the incubated cell possession area.

FIG. 9 shows an example of rate-of-change graph of an incubated cell possession area when a cancer cell is incubated with anticancer drug administration provided. The vertical axis of FIG. 9 shows the possession area of the incubated cell (number of cancer cells) and the horizontal axis of FIG. 9 shows time elapse. Further, FIG. 9 shows an example in which the incubation is carried out in three incubation containers with anticancer drug different from one another administered, respectively.

Here, the graph of FIG. 9 shows that the anticancer drug performs an effective action when "incubated cell possession area" reduces. Further, as the slope of the graph in FIG. 9 (rate of change of an incubated cell possession area) becomes steeper, the anticancer drug is found to perform a more effective action. Further, when focusing on a time when the rate of change of an incubated cell possession area becomes higher in FIG. 9, it is found that the onset time of the drug power can be estimated.

Note that, for another example, the search processing section 46 and the computing section 47 can estimate the time of the confluence using above "rate of change of an incubated cell possession area". A cell division frequency has a correlation with the cell possession area, and the cell division frequency decreases as the possession area becomes larger. Accordingly, it is found that the incubated cell comes close to the confluence when the above rate of change of possession area becomes lower than a certain value.

Specifically, when instructed to predict the confluence, the computing section 47 obtains "rate of change of an incubated cell possession area" in the above described manner. Then, the computing section 47 assumes that the subsequent rate-of-change transitions in the value of "rate of change of an incubated cell possession area" obtained from the image analyzing data, and obtains date and time when this rate of change becomes lower than a certain value. After that, the search processing section 46 causes the monitor 41a or the like to display the date and time obtained by the computing section 47 as a predictive time point of the confluence. Thereby, it is possible to predict the confluence preliminarily and user convenience is further improved.

(6) Case of the Searching Condition "Rate of Change in a Ratio of a Single Cell to a Two-Coupled Cell Among Incubated Cells"

In this case, first the search processing section 46 designates the plurality of image files taken temporally for the same image object (e.g., first image file and last (latest) image file) as search objects for each of the incubation containers 30 using the identification data.

Next, the computing section 47 computes plural values for "a ratio of a single cell to a two-coupled cell among incubated cells" from the image files of the search objects, respectively, and obtains "rate of change in a ratio of a single cell to a two-coupled cell among incubated cells" using these computation results.

Then, the search processing section 46 causes the monitor 41a or the like to display a list screen which shows the rate of change in a ratio of a single cell to a two-coupled cell among incubated cells for each of the incubation containers 30 in the temperature-controlled room 15. The list screen in this case has a display format approximately in common with that of FIG. 8 and explanation will be omitted. By such display of "rate of change in a ratio of a single cell to a two-coupled cell among incubated cells", it is possible to analyze the cell division frequency in each of the incubation containers 30 and the user can easily carry out the evaluation of the cell incubation state (e.g., determination for medicine screening).

Here, "a ratio of a single cell to a two-coupled cell among incubated cells" represents a cell division frequency at a certain time. Accordingly, by using temporal analysis result of "a ratio of a single cell to a two-coupled cell among incubated cells", it becomes possible to predict a time of a high cell division frequency and a time of a minus rate of change (division cycle).

Specifically, when instructed to predict the division cycle, the computing section 47 obtains "rate of change in a ratio of a single cell to a two-coupled cell among incubated cells" in the above manner. Then, the computing section 47 assumes that the subsequent rate-of-change transitions in the pattern of "rate of change in a ratio of a single cell to a two-coupled cell among incubated cells" obtained from the image analyzing data, and obtains date and time when the rate of change becomes a desired rate designated by the user. After that, the search processing section 46 causes the monitor 41a or the like to display the date and time obtained by the computing section 47 as a prediction result.

Figure 10:
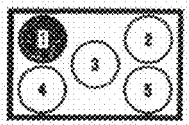
FIG. 10 is a diagram showing a display screen of a predicted division cycle.

Note that FIG. 10 shows a screen displaying the time of the minus rate of change for each of the incubation containers. Thereby, it becomes easy to perform scheduling of the cell incubation by the division cycle prediction and user convenience is further improved.

(7) Case of the Searching Condition "Rate of Change of a Barycentric Point Individual Area"

In this case, first the search processing section 46 designates the plurality of image files taken temporally for the same image object (e.g., first image file and last (latest) image file) as search objects for each of the incubation containers 30 using the identification data.

Next, the computing section 47 computes an area ratio of a cell cluster (colony) and a cell except the cell cluster from the meta data of "barycentric point individual area" for each of the image files of the search objects. After that, the computing section 47 obtains a change of each of the above area ratios and determines the obtained result to be the rate of change of the barycentric individual area.

Then, the search processing section 46 causes the monitor 41a or the like to display a list screen which shows the rate of change of the barycentric point individual area for each of the incubation containers 30 in the temperature-controlled room 15. The list screen in this case has a display format approximately in common with that of FIG. 8 and explanation will be omitted. By such display of "rate of change of a barycentric point individual area", it is possible to easily grasp a colony forming state and the growth thereof in each of the incubation containers 30.

Note that, by using "rate of change of a barycentric point individual area", it becomes possible to predict the generation of a colony in the incubation container. Specifically, when instructed to predict the generation of the colony, the computing section 47 obtains "rate of change of a barycentric point individual area" in the above manner. Then, the computing section 47 assumes that the subsequent rate-of-change transitions in the pattern of "rate of change of a barycentric point individual area" obtained from the image analyzing data, and obtains date and time when the rate becomes a desired rate designated by the user. After that, the search processing section 46 causes the monitor 41a or the like to display the date and time obtained by the computing section 47 as a prediction result. Thereby, it becomes possible to predict the generation time of the colony and user convenience is further improved.

Step S203: The CPU 44 determines whether or not to have received an instruction input for the detailed display including the designation of the incubation container 30 or the microscope observing image, from the user. If the above input has been received (YES side), the process goes to S204. On the other hand, if the above input has not been received (NO side), the process goes to S205.

Step S204: The CPU 44 causes the monitor 41a of the operation panel 41 (or monitor of the computer 52) to display the detailed display screen (FIG. 11) for the incubation container 30 or the microscope observing image designated in S203. This detailed display screen displays a predetermined microscope observing image (microscope observing image at default), a graph showing a temporal parameter change extracted by the CPU 44 from each of the image files by the use of the identification data, and a distribution chart showing the size and shape of each cell. Further, the detailed display screen also displays an icon for identifying the position of the container, in consideration of a case in which the incubation container 30 includes a plurality of small containers.

Figure 11:
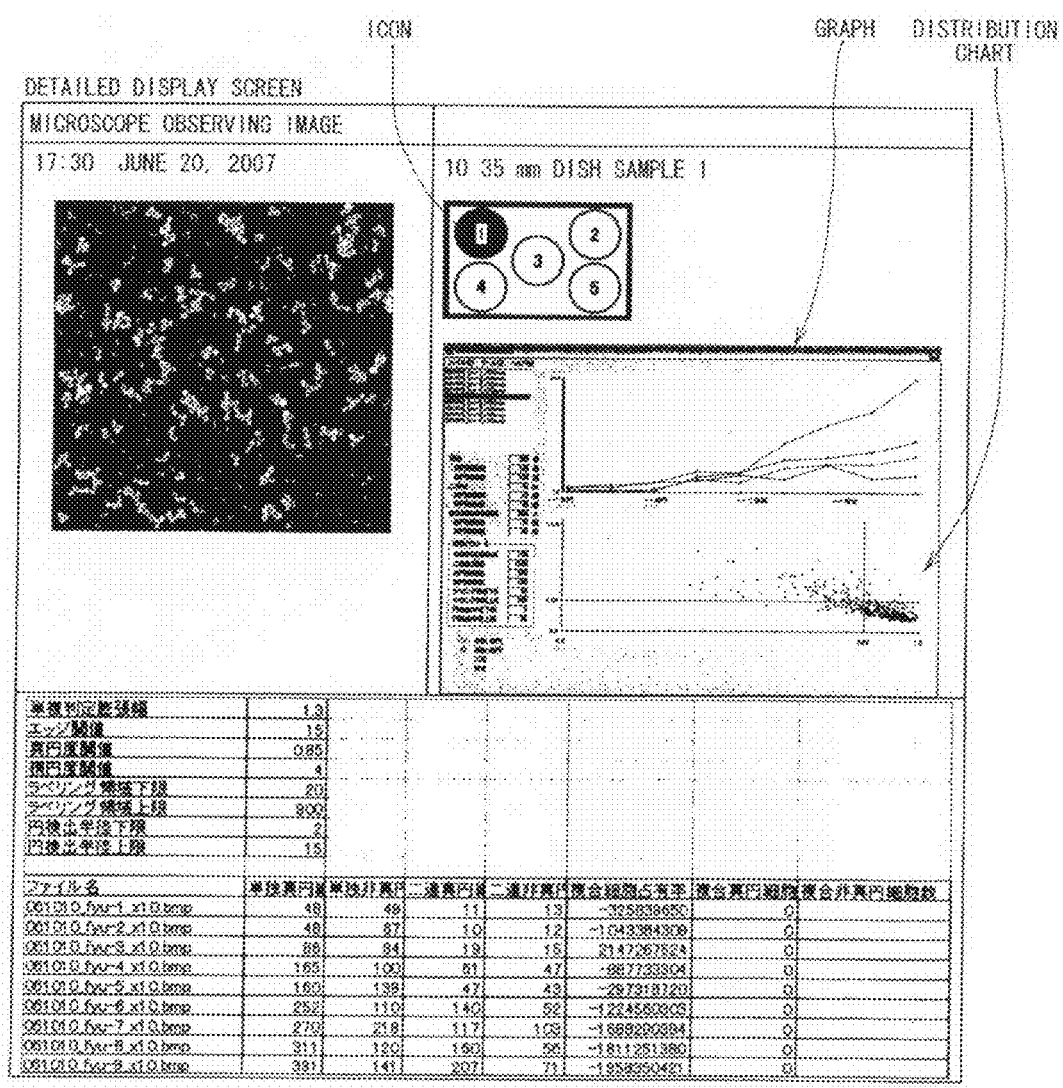
FIG. 11 is a diagram showing a detailed display screen of S204.

Here, FIG. 11 displays the above graph in the right center of the screen. The vertical axis of this graph shows the number of cells and the horizontal axis shows time elapse. Then, the four polygonal lines in FIG. 11 show the changes in the numbers of "two-coupled cells", "composite cells", "circular single cells", and "non-circular single cells", respectively, in this order from above.

Further, FIG. 11 displays the above distribution chart on the lower side of the graph. The vertical axis of this distribution chart shows the cell size. Further, the horizontal axis of the distribution chart shows the circularity of the cell. Note that, in a typical incubation case, it is considered that a smaller cell size and a higher cell circularity (i.e., more plots in the fourth quadrant in the distribution chart) shows a preferable incubation state.

Step S205: The CPU 44 determines whether or not to have received an input from the user for carrying out the search again. If the above input has been received (YES side), the CPU 44 returns to S201 and repeats the above operations. On the other hand, if the above input has not been received (NO side), the CPU 44 goes to S206.

Step S206: The CPU 44 determines whether or not to have received a termination operation of the search processing. If the above input has been received (YES side), the CPU 44 terminates the sequence program of the search processing and goes to a waiting state. On the other hand, if the above input has not been received (NO side), the CPU 44 returns to S205 and repeats the above operation. With that, the explanation of FIG. 7 is finished.

An embodiment generates the image file associating the identification data indicating the incubation container with the image analyzing data for the microscope observing image data and, in the searching, searches for the desired incubation container or observing image using the image analyzing data and the identification data. Thereby, it becomes easy to search for the microscope observing image or the analysis information generated in the culture apparatus, and user convenience is improved.

(Application Example of Culture Information Search Processing)

Next, as one of application examples for the culture information search processing, an example for differentiation induction of a stem cell will be described. This example assumes that a stem cell such as an embryonic stem cell (ES cell) and an induced pluripotent stem cell (iPS cell) is incubated in an incubation container.

For example, when a stem cell is incubated in the field of regeneration medicine, it is required to carry out the differentiation induction from the stem cell to a cell corresponding to a therapeutic objective region (nerve cell or the like). Then, for the incubation of the stem cell, it becomes extremely important to establish an efficient incubation method when a specific cell is differentiation-induced from the stem cell and to manage the incubation protocol of the incubation thereof.

Here, when the incubation method of the stem cell is determined to be appropriate or not, the cell form and the rate of change thereof become important factors. It is known that, while a cell has a spindle shape in the state of the stem cell, the cell comes to have a special shape having a constriction (tow-coupled state) when the cell is differentiation-induced. Accordingly, by focusing on the cell form, it is possible to grasps the number of cells differentiation-induced from the stem cell. Then, when the differentiation induction of the stem cell occurs more frequently than a certain level and also medium replacement or passage is carried out by selecting an incubation container which has a high productivity of the differentiation-induced cell, it is possible to incubate a target cell more efficiently.

Accordingly, when the stem cell is incubated by a plurality of different incubation methods in the incubator of the above embodiment, it becomes possible to obtain an efficient incubation method of the stem cell by carrying out the search processing using the cell form and the rate of change thereof as the searching conditions.

Figure 7:
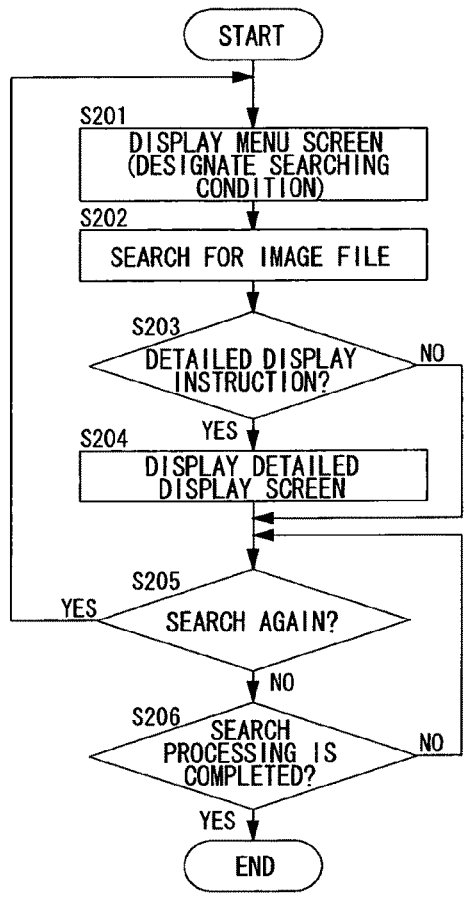
FIG. 7 is a flowchart illustrating search processing of culture information in the embodiment.

FIG. 12 shows a display example of a menu screen in S201 of FIG. 7. In this example, the user designates "number of cells after differentiation induction (two-coupled cells)" as a first searching condition regarding the cell form and designates "increase rate of cells after differentiation induction (two-coupled cells)" as a second searching condition regarding the rate of change on the menu screen.

At this time, on the menu screen, the user can designate at least one of an upper limit value and a lower limit value regarding the first searching condition and second searching condition for the search object, respectively. For example, when the lower limit value is designated for "increase rate of cells after differentiation induction", an incubation container having an increase rate lower than the lower limit value is rejected from a search result and thereby the user can extract an incubation container having a preferable incubation state by the search processing. On the other hand, when the upper limit value is designated for "increase rate of cells after differentiation induction", an incubation container having an increase rate higher than the upper limit value is rejected from the search result and thereby the user can extract an incubation container having an undesirable incubation state by the search processing.

Then, in S202 of FIG. 7, the search processing section 46 searches for the image file in the memory section 43 using the first searching condition and the second searching condition input on the menu screen as keys.

In the above search processing, first the search processing section 46 designates each of two image files taken time-sequentially within the same viewing range for the same incubation container 30 as a search object using the identification data. Next, the computing section 47 obtains "increase rate of cells after differentiation induction" using the ratio of "number of coupled cells" values each obtained from the image file of the search object. After that, the search processing section 46 changes one of the image files in the search objects and obtains "increase rate of cells after differentiation induction" at a different time range. By repeating this operation, the computing section 47 generates data indicating a temporal change of "increase rate of cells after differentiation induction" for one incubation container 30.

When the image files exist for the plurality of incubation containers 30, respectively, the search processing section 46 obviously obtains "increase rate of cells after differentiation induction" for each of the incubation containers. Note that, when one incubation container 30 includes a plurality of independent small containers, the search processing section 46 obtains "increase rate of cells after differentiation induction" for each of the small containers.

After that, the search processing section 46 outputs and displays the above search result on the monitor 41a or the like. FIG. 13 shows an example of the search result screen. This search result screen of FIG. 13 shows respective icons indicating the incubation containers in a state sorted according to an extent of meeting the search condition. Note that, it is assumed that in the example of FIG. 13, the incubation container, which has a larger number of cells after the differentiation induction and a higher increase rate of the cells after the differentiation induction, is displayed on an upper side of the screen.

Figure 14:
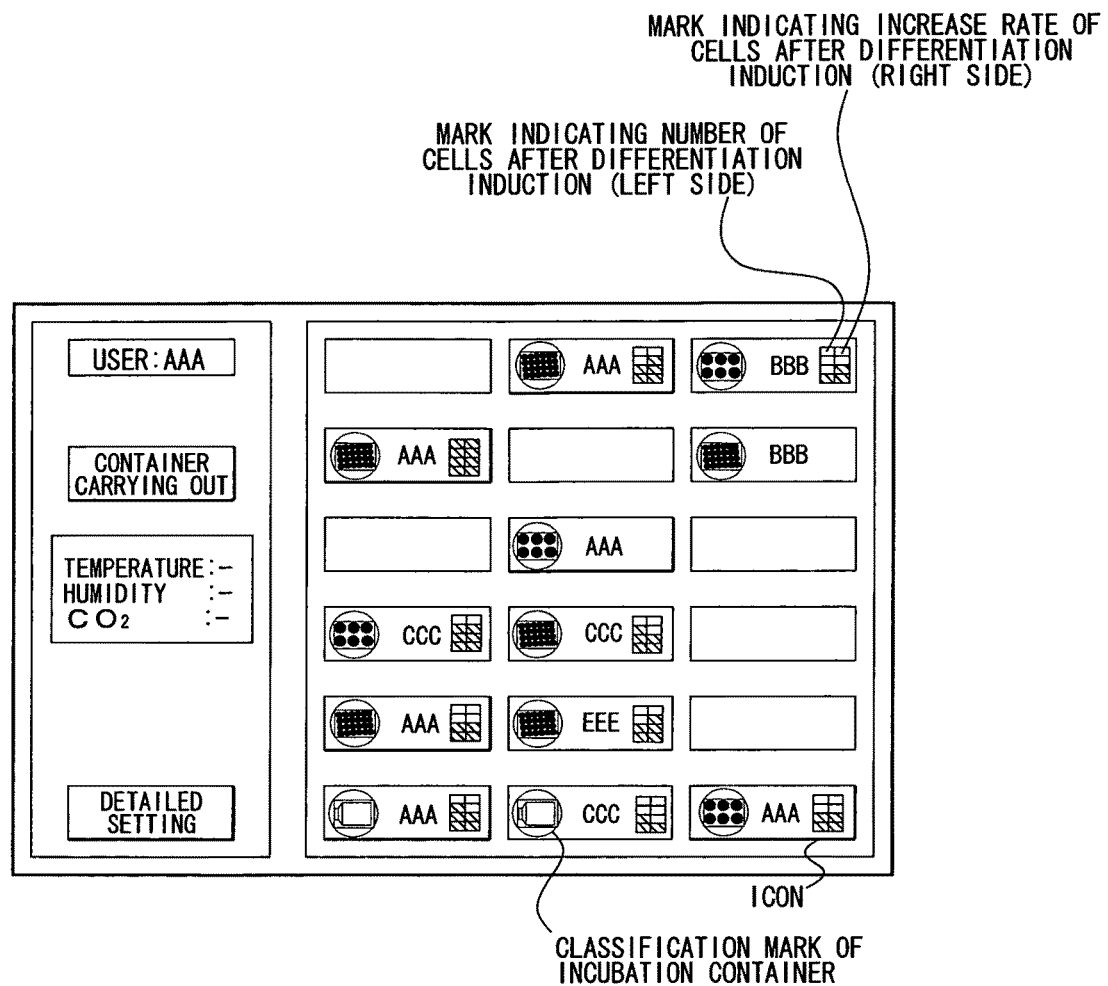
FIG. 14 is a diagram showing another example of the search result screen.

Further, FIG. 14 shows an example of a list screen showing the search result by the number and the increase rate of the cells after the differentiation induction. The list screen of FIG. 14 displays the incubation container 30 in the temperature-controlled room 15 by an icon in the GUI format as in the example of FIG. 8. Further, the screen of FIG. 14 displays a mark indicating a maximum value of the number of cells after the differentiation induction and a mark indicating a maximum value of the rate of change in the number of cells after the differentiation induction on each of the icons. Note that, in each of the marks on the icon of FIG. 14, a bar display in the mark is positioned in an upper side as each of the maximum values exhibits a higher value. In this screen of FIG. 14, it is easy for the user to confirm the differentiation induction state of the stem cell in each of the incubation containers 30.

Then, when the user designates the icon on the screen of FIG. 13 or FIG. 14, the CPU 44 causes the display of the monitor 41*a* or the like to morph into the detailed display screen of FIG. 11. At this time, the CPU 44 may display the temporal change of "increase rate of cells after differentiation induction" by a graph on the detailed display screen of FIG. 11. Thereby, it becomes easy for the user to confirm the differentiation induction state of the stem cell in each of the incubation containers 30.

Further, the search processing section 46 may select the data exhibiting a more preferable differentiation induction state of the stem cell among the data sets of the incubation container 30 extracted by the searching and may register incubation environment information for the incubation container 30 (e.g., various kinds of data such as temperature, humidity, kind of added medicine, and medium replacement timing) in the memory section 43. Thereby, the user comes to easily realize a preferable incubation condition for the differentiation induction of the stem cell, by causing the CPU 44 to read out the incubation environment information registered in the memory section 43 and referring to the incubation environment information. Note that the search processing section 46 may register the incubation environment information of the incubation container 30 having the highest rank in the search result of FIG. 13, for example, in the memory section 43, or may register the incubation environment information according to the user input in the memory section 43.

Further, when the CPU 44 carries out sequential search processing during an incubation period using "number of cells after differentiation induction" and "increase rate of cells after differentiation induction", the user can confirm the incubation state of the stem cell almost in real time.

Further, the CPU 44 can automatically extract the incubation container which comes into a predetermined state during the incubation period using the search processing result. In this case, the user preliminarily inputs a threshold value (at least one of a upper limit value and a lower limit value) for the searching condition "number of cells after differentiation induction" or "increase rate of cells after differentiation induction" into the CPU 44, and also the search processing section 46 carries out the above search processing at predetermined intervals during the incubation period of the stem cell. Then, when the search result exceeds the above threshold range, the CPU 44 notifies the user by means such as a display output to the monitor 41*a* or the like and E-mail transmission to a preliminarily registered mail address. Thereby, an embodiment allows the user to manage the incubation of the stem cell further more easily.

(Supplement to the Embodiment)

(1) In the above embodiment, the search processing section 46 may search for the incubation container or the microscope observing image using the other information added to the image file as the meta data (parameter other than the standard statistical amount of image analyzing data, the cell morphology information, and the image untidiness information).

(2) Further, in the above embodiment, an incubator system may be configured with the computer 52 coupled to the control unit 14 and causes the computer 52 to execute a program to realize the functions of the analysis processing section 45, the search processing section 46, and the computing section 47. Moreover, while an example is described in an embodiment for realizing the analysis processing section 45, the search processing section 46, and the computing section 47 in software, these sections may be realized by hardware such as an ASIC.

(3) In the above application example of the search processing for culture information, an example of performing the search using "number of cells after differentiation induction" and "increase rate of cells after differentiation induction" is described. However, "possession area of a cell after differentiation induction", for example, may be set to be the first searching condition in this application example.

The many features and advantages of the embodiment are apparent from the detailed specification and, thus, it is intended by the appended claims to cover all such features and advantages of the embodiment that fall within the true spirit and scope thereof. Further, since numerous modifications and changes will readily occur to those skilled in the art, it is not desired to limit the inventive embodiment to the exact construction and operation illustrated and described, and accordingly all suitable modifications and equivalents may be resorted to, falling within the scope thereof.

What is claimed is:

1. A culture apparatus, comprising:
    a temperature-controlled room accommodating an incubation container incubating samples and maintaining inside thereof in a predetermined environment condition;
    an imaging section imaging the samples of the incubation container in the temperature-controlled room and generating data of a plurality of observing images;
    an image analyzing section performing an image analyzing process on the data of the plurality of the observing images obtained by imaging the incubation container at different times and generating image analyzing data including morphologic information which indicates incubation states of the samples and rate-of-change information regarding the morphological information based on the observing images;
    a memory section storing a correspondence relationship between the incubation container and the image analyzing data;
    an input section receiving an input of a first searching condition regarding the morphological information and an input of a second searching condition regarding the rate-of-change information; and
    a search processing section conducting a search for an incubation container which meets the first searching condition and the second searching condition and determining whether or not the environment condition of a sample accommodated in the incubation container is acceptable based on a ranking of environment information for each incubation container from among a plurality of incubation containers being accommodated in the temperature-controlled room based on the image analyzing data of the memory section.

2. The culture apparatus according to claim 1, wherein the morphological information includes information indicating at least one of a possession area of the samples, a category of a form of the samples, a barycentric point of each of the samples, and an area of each of the samples in the observing images.

3. The culture apparatus according to claim 1, wherein the input section receives at least one of an upper limit and a lower limit of a rate of change in the morphological information as the second searching condition.

4. The culture apparatus according to claim 1, wherein the search processing section causes the memory section to store an incubation environment information which corresponds to a specific incubation container extracted by the search from a plurality of incubation containers.

5. The culture apparatus according to claim 1, wherein
the search processing section performs display output indicating a position of the incubation container which meets the first searching condition and the second searching condition.

6. The culture apparatus according to claim 1, wherein
the incubation container includes a plurality of independent small containers;
the image analyzing section, when the incubation container includes a plurality of incubation regions by the small containers, generates the image analyzing data for each of the incubation regions, and
the search processing section conducts the search on each of the incubation regions.

7. The culture apparatus according to claim 1, further comprising
an estimating section obtaining a predictive value of a morphological change of the samples included in the incubation container based on the rate-of-change information, wherein
the search processing section, when a standard value of the morphological change is designated as the first searching condition and the second searching condition, searches for a time when the predictive value obtained for the incubation container meets the standard value and output and display a result of the search.

8. A culture information management method using a computer coupled to a culture apparatus including a temperature-controlled room accommodating an incubation container incubating samples and maintaining the inside thereof in a predetermined environment condition, and an imaging section imaging the samples of the incubation container in the temperature-controlled room and generating data of a plurality of observing images, the culture information management method comprising:
performing an image analyzing process on the data of the plurality of the observing images obtained by imaging the incubation container at different times and generating image analyzing data including morphologic information which indicates incubation states of the sample and rate-of-change information regarding the morphological information based on the observing images;
storing a correspondence relationship between the incubation container and the image analyzing data to a storage medium;
receiving an input of a first searching condition regarding the morphological information and an input of a second searching condition regarding the rate-of-change information by the computer; and
conducting a search for an incubation container which meets the first searching condition and the second searching condition and determining whether or not the environment condition of a sample accommodated in the incubation container is acceptable based on a ranking of environment information for each incubation container from among a plurality of incubation containers being accommodated in the temperature-controlled room based on the image analyzing data of the storage medium.

9. A non-transitory computer readable medium storing program causing a computer to execute each process of the culture information management method according to claim 8.

* * * * *